(12) United States Patent
Le Couëdic et al.

(10) Patent No.: US 10,543,023 B2
(45) Date of Patent: Jan. 28, 2020

(54) DEVICE AND SYSTEM FOR FIXING A SPINAL VERTEBRA TO A ROD

(71) Applicant: IMPLANET, Martillac (FR)

(72) Inventors: Régis Le Couëdic, Bordeaux (FR); Denis Pasquet, Aix-en-Provence (FR)

(73) Assignee: IMPLANET, Martillac (FR)

( * ) Notice: Subject to any disclaimer, the term of this patent is extended or adjusted under 35 U.S.C. 154(b) by 113 days.

(21) Appl. No.: 15/566,612

(22) PCT Filed: Apr. 14, 2016

(86) PCT No.: PCT/FR2016/050867
§ 371 (c)(1),
(2) Date: Oct. 13, 2017

(87) PCT Pub. No.: WO2016/166482
PCT Pub. Date: Oct. 20, 2016

(65) Prior Publication Data
US 2018/0132905 A1      May 17, 2018

(30) Foreign Application Priority Data
Apr. 17, 2015   (FR) ..................... 15 53428

(51) Int. Cl.
*A61B 17/70*      (2006.01)
(52) U.S. Cl.
CPC ...... *A61B 17/7053* (2013.01); *A61B 17/7037* (2013.01)
(58) Field of Classification Search
CPC . A61B 17/701; A61B 17/7019; A61B 17/702; A61B 17/7022; A61B 17/7026; A61B 17/7029; A61B 17/7031; A61B 17/7083; A61B 17/82; A61B 17/842; A61B 17/8869; A61B 17/7014; A61B 17/7041;
(Continued)

(56) References Cited

U.S. PATENT DOCUMENTS 5,383,905 A * 1/1995 Golds ................ A61B 17/0487
24/136 L
6,176,861 B1 * 1/2001 Bernstein ........... A61B 17/7007
606/246
(Continued)

FOREIGN PATENT DOCUMENTS

| EP | 2422728 A1 | 2/2012 |
|---|---|---|
| EP | 2762095 A1 | 8/2014 |
| WO | 2009/144663 A1 | 12/2009 |

OTHER PUBLICATIONS

Written Opinion of the International Searching Authority dated Sep. 16, 2016, issued in corresponding International Application No. PCT/FR2016/050867, filed Apr. 14, 2016, 6 pages.
(Continued)

*Primary Examiner* — Lynnsy M Summitt
(74) *Attorney, Agent, or Firm* — Christensen O'Connor Johnson Kindness PLLC

(57) ABSTRACT

A device and a system comprising such a device, for fixing a spinal vertebra to a rod. The device comprises a pedicle screw and an anchor lug for fixing the screw to the rod. The device also comprises a flexible strip for connection to the vertebra, a ring secured to the lug, and means secured to said ring, for adjustably locking the flexible strip in relation to the anchor lug.

12 Claims, 5 Drawing Sheets

(58) Field of Classification Search
CPC ............ A61B 17/7043; A61B 17/7044; A61B 17/7053
See application file for complete search history.

(56) References Cited

U.S. PATENT DOCUMENTS

| | | | | |
|---|---|---|---|---|
| 7,335,201 | B2* | 2/2008 | Doubler | A61B 17/7035 606/264 |
| 7,678,136 | B2* | 3/2010 | Doubler | A61B 17/7007 606/246 |
| 8,518,080 | B2* | 8/2013 | Egli | A61B 17/705 606/246 |
| 8,709,049 | B2* | 4/2014 | Klein | A61B 17/7007 606/259 |
| 8,926,668 | B2* | 1/2015 | Douget | A61B 17/7032 606/246 |
| 9,402,666 | B2* | 8/2016 | Al Shail | A61B 17/7053 |
| 9,456,852 | B2* | 10/2016 | Beyar | A61L 27/446 |
| 9,510,866 | B2* | 12/2016 | Hammer | A61B 17/7032 |
| 2010/0094345 | A1* | 4/2010 | Saidha | A61B 17/7052 606/250 |
| 2011/0245875 | A1* | 10/2011 | Karim | A61B 17/7037 606/263 |
| 2012/0271356 | A1* | 10/2012 | Ramsay | A61B 17/7032 606/278 |
| 2018/0078286 | A1* | 3/2018 | Le Couedic | A61B 17/7043 |

OTHER PUBLICATIONS

International Preliminary Report of Patentability dated Oct. 17, 2017, issued in corresponding International Application No. PCT/FR2016/050867, filed Apr. 14, 2016, 1 page.

International Search Report dated Sep. 16, 2016, issued in corresponding International Application No. PCT/FR2016/050867, filed Apr. 14, 2016, 3 pages.

Written Opinion of the International Searching Authority dated Sep. 16, 2016, issued in corresponding International Application No. PCT/FR2016/050867, filed Apr. 14, 2016, 7 pages.

* cited by examiner

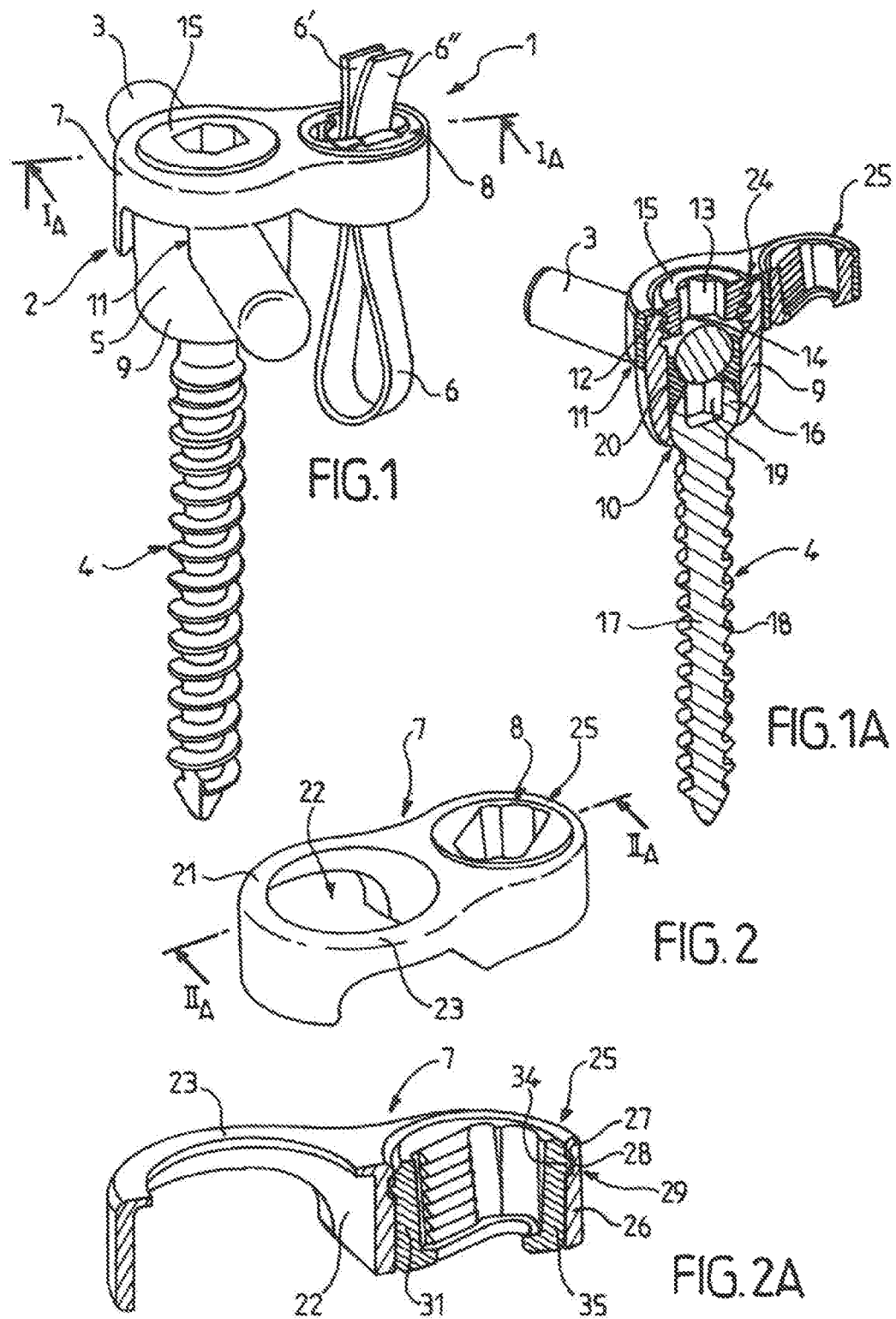

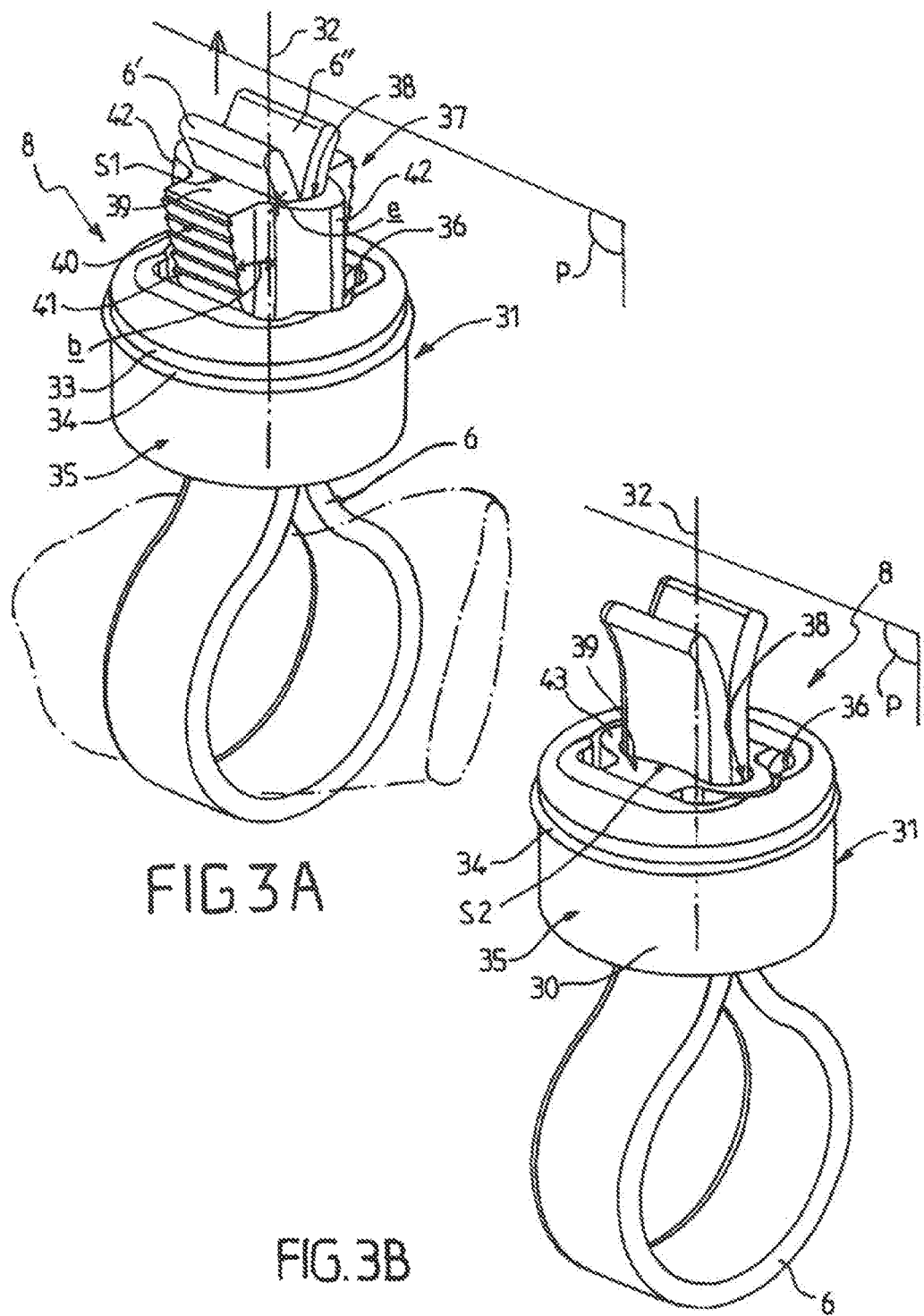

DEVICE AND SYSTEM FOR FIXING A SPINAL VERTEBRA TO A ROD

The present invention relates to a device for fixing a spinal vertebra to a rod, having a pedicle screw and a lug for fixing the screw to the rod.

It also relates to a system provided with a rod and with at least one such device.

It also relates to a method for fixing a rod to a vertebra, in which method a pedicle screw is screwed into the vertebra, the rod is slid through a lug for fixing the screw to the rod, and a compression screw is screwed onto the rod through the upper part of the lug.

It has a particularly important but not exclusive application in the field of straightening the vertebral column of a patient having an abnormal curvature.

In order to straighten the arrangement, it is known to bring the lateral margins of the vertebrae on either side of the vertebral column together, by means of a rod connecting them, either with screws, which are inserted into the vertebrae themselves, or hooks, which are introduced along the spinal canal.

However, these devices are not entirely satisfactory.

It may in fact be the case that the bone of the vertebra is not of a good quality, for example on account of osteoporosis.

In the case of using a screw, the latter then has to be longer in order to improve the fixation. In this case, however, the surgeon is uncertain as to whether the pedicle protrudes from the vertebra once screwed.

Similarly, in the case of using hooks, this is delicate and entails a risk of an accident that may lead to paralysis of the patient.

Another way of dealing with the poor quality of the bone of a vertebra is to transfer the fixation to the adjacent vertebra of better quality. However, this involves fusing the vertebrae to each other, which promotes what is called the hinge syndrome, in which all of the stresses are transferred to a location above the vertebrae that have been fused to each other.

To overcome these disadvantages, systems have been proposed (FR 2 954 905, EP 2 762 095) using a flexible link for fixing the vertebra to a linking piece, which is itself fixed to the rod.

Although such systems make it possible to obtain progressive and effective clamping, there are some cases, especially when the rod is made of non-metallic material, where they may cause the flexible band to lose tension over the course of time.

Nor do they make it possible to avoid twisting of the band.

The present invention aims to overcome the disadvantages of the prior art.

To do so, it proceeds from the concept of simultaneously using a pedicle screw and a flexible link for fixing the vertebra to a component fixed to the head of the pedicle screw.

The length of the screw can thus be kept to a reasonable size, even in cases of poor quality of the bone.

The present invention therefore aims to make available a device, a system and a method for fixing a spinal vertebra to a rod in a manner that is improved over the prior art in terms of meeting the requirements that arise in practice, especially in that it will permit excellent fixing of the lug while keeping costs under control and ensuring great flexibility and ease of fitting by the surgeon.

To this end, the invention proposes in particular a device for fixing a spinal vertebra to a rod, having a pedicle screw, a lug for fixing the screw to the rod, and a flexible band for connection to the vertebra, characterized in that it has an attached ring rigidly connected to the lug, and means rigidly connected to said ring for adjustably blocking the flexible band with respect to the fixing lug.

Advantageously, the lug is formed by a body rigidly connected to and forming a continuation of the head of the pedicle screw (or upper end opposite the thread of the screw) to which the ring is fixed.

More precisely, the ring rigidly connected to the lug is, for example, initially independent of the latter and is subsequently fixed thereto removably or non-removably.

In advantageous embodiments, use is moreover and/or furthermore made of one or more of the following provisions:

The blocking means are movable in rotation with respect to the ring, whereby it is possible to avoid twisting of the band;

Advantageously, they are inserted into a lateral cylindrical orifice of the ring (offset laterally in relation to the screw and/or to the body of the lug), with which said means cooperate by slight friction.

The blocking means are then free in rotation about the axis of the orifice, advantageously parallel to the axis of the screw and of the body.

The body has a cup shape, designed to be traversed laterally by the rod perpendicularly with respect to the pedicle screw, and is provided with an internal thread in its upper part, for fixing the rod by way of a compression screw, and the ring comprises a first through-orifice which can be clipped or fixed by deformation onto the upper periphery of the lug, and a second lateral through-orifice for supporting the blocking means;

The lug comprises an upper part which is cylindrical or shaped as a portion of a cylinder with a first diameter, and the first orifice is cylindrical with a diameter matching the first diameter, with which it is designed to cooperate by friction, before the compression screw is screwed in, and to become blocked by slight expansion of the lug during the clamping.

The expansion is, for example, 0.2 mm in diameter, which is sufficient to block all movement of the ring on the lug with which it is in cylinder/cylinder contact.

The lug comprises a frustoconical upper part, the first orifice having a frustoconical shape matching said upper part with which it cooperates by friction, and comprises at least one vertical blocking stub in the bottom portion;

The lug comprises an upper part provided with a retaining groove or rib, and the first through-orifice of the ring is provided with a rib or groove of corresponding shape designed to be engaged with force one inside the other;

The blocking means comprise a rigid base body with a through-orifice, and a holding component that is insertable into said orifice, the holding component being at least partially in the shape of a squeezable wedge comprising a central bore for passage of the opposite end portions of the band, said bore having a cross section that is deformable between a first cross section for free passage of the end portions when the component has not been inserted into the orifice, and a second cross section for blocking said end portions by compression when the component is entirely or substantially entirely inserted into the orifice.

Advantageously, the blocking is effected by non-return teeth, for example having the shape of a V.

The second orifice of the ring comprises a retaining rib or groove, and the holding component comprises a complementary groove or rib designed to be clipped then blocked vertically upward with the rib or groove of the second orifice of the ring.

Such an arrangement permits the rotation of one with respect to the other.

The pedicle screw has a round or oblong head mounted pivotably in rotation in the lower part of the lug, and the lug has a joining structure between the cylindrical wall of the rod and said screw head.

The joining structure matches the shape of the rod on one side and of the head on the other.

The invention also relates to a system comprising a rod and at least one device as described above.

Advantageously, the invention also relates to a method for fixing a rod to a vertebra using a device as described above.

It also relates to a method for fixing a rod to a vertebra in which a pedicle screw provided with a lug on the rod is screwed into the vertebra, the rod is slid through the lug, and a compression screw is screwed onto the rod through the upper part of the lug, characterized in that, before screwing in the compression screw, a flexible band is passed around said vertebra, a first through-orifice of a ring is clipped onto the upper periphery of the lug, said ring being able to be clipped or fixed by deformation on said upper periphery, said ring comprising a second lateral through-orifice for supporting adjustable means for blocking the flexible band, said blocking means being movable in rotation with respect to the ring and/or the fixing lug, the flexible band is placed on the vertebra and in the blocking means, one starts to tension said flexible band, the free rotation making it possible to limit the twisting stresses of the band, after which one tensions the whole assembly before finally blocking the compression screw and the band with respect to the lug.

Advantageously, the blocking means comprise a rigid base body with a through-orifice, and a holding component insertable into said orifice, the holding component being at least partially in the shape of a squeezable wedge comprising a central bore for passage of the opposite end portions of the band, said bore having a cross section that is deformable between a first cross section for free passage of the end portions when the component has not been inserted into the orifice, and a second cross section for blocking said end portions by compression when the component is entirely or substantially entirely inserted into the orifice, the band is inserted into the base body and the holding component and, after tensioning, and in order to block the band against movement, the component is inserted entirely into the body.

The invention will be better understood on reading the following description of embodiments given below as non-limiting examples. The description makes reference to the accompanying drawings, in which:

FIG. 1 is a perspective axonometric view of a fixing device and/or system according to a first embodiment of the invention.

FIG. 1A is a sectional view along $I_A$-$I_A$ in FIG. 1, without the flexible band.

FIG. 2 is a perspective view of the kind of ring used in the device of FIG. 1.

FIG. 2A is a sectional view along $II_A$-$II_A$ in FIG. 2.

FIGS. 3A and 3B are perspective views of the blocking means according to an embodiment of the invention, before insertion (FIG. 3A) and after complete insertion (FIG. 3B) of the holding component into the base body.

Figure 4:
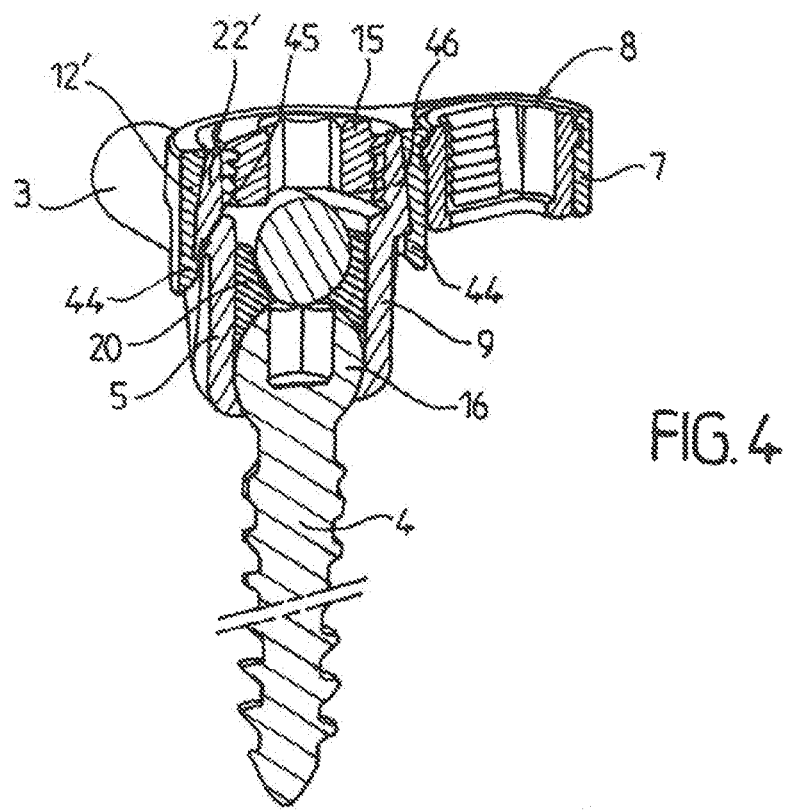
FIG. 4 is a longitudinal sectional view of a device and/or system according to another embodiment of the invention.

FIG. 1 shows a system 1 comprising a device 2 for fixing a vertebra (not shown) to a rod 3, having a pedicle screw 4 and a lug 5 for fixing the screw to the rod.

The device 2 has a flexible and flat band 6, for example of braided polyester, for example 1 to 3 mm in thickness and 6 mm in width, and has a loop for fixing to the vertebra, for example around one of the transverse or spinous processes (not shown).

The loop is formed by bringing together the end portions 6' and 6" of the band.

The device 2 has a ring 7 rigidly connected to the lug 5, and means 8 for adjustably blocking the flexible band with respect to the lug 5, by blocking these two end portions 6, 6', as will be described in more detail below.

Referring also to FIG. 1A, the lug 5 comprises a substantially cylindrical cup-shaped body 9 recessed in its lower part or bottom 10 to allow the pedicle screw 4 to pass through, and it has two lateral notches 11, open toward the top, for the lateral passage of the rod 3 which is engaged therein.

The body 9, made of titanium for example, is cylindrical in its upper part 12 and widened inward in its lower part.

The body 9 comprises a cylindrical recess 13 in which the screw is passed and blocked in the axial direction. The upper part 12 comprises an internal thread 14 for fixing the rod, which has been introduced into the lateral notches 11, by a compression screw 15, which will thus press the rod onto the head 16 of the pedicle screw 4.

The latter comprises a screw body 17 provided with a screw thread 18 of a type known per se.

The head 16 is provided with a socket 19 to permit screwing by a tool. It is partially spherical and bears on the bottom 10 of the cup of the body 9 of the lug with which it cooperates frictionally in rotation and in longitudinal abutment.

After the pedicle screw 4 previously introduced into the lug 5 has been screwed in, and after a joining/guiding/supporting component 20 has been introduced above the screw head, which component 20 has a ring shape at one side (screw head) and is semicylindrical at the other side (rod), and after the rod 3 has been introduced, the ring 7 is put in place.

The ring 7 is a component made of titanium for example, in the shape of a flattened haricot bean, with a horizontal longitudinal section forming the shape of an 8, of which the loops are not of the same dimensions.

It comprises (cf. FIGS. 2 and 2A) a first substantially cylindrical portion 21 provided with an internal cylindrical bore 22 or first orifice comprising a narrowed upper part 23 which, with the top 24 of the lug 5, forms a block against axial movement.

The internal bore 22 cooperates frictionally, by cylinder/cylinder contact, with the outer surface of the cylindrical upper part 12 of the lug.

Once the ring has been placed with friction onto the upper part of the lug, the clamping screw 15 is screwed in.

This screwing-in, for which the head of the screw 15 is designed, provides a slight expansion of the volume that it occupies during the clamping, for example of the order of 0.2 mm, which deforms the bore of the lug by lateral compression, which blocks all movement of the ring with respect to the lug.

Laterally with respect to the first orifice, the ring 7 comprises a second through-orifice 25 for supporting the blocking means 8.

The second orifice 25 (see FIG. 2A) is cylindrical with an axis parallel or substantially parallel to that of the first orifice and/or the pedicle screw. It comprises a lower portion 26 and an upper portion 27, the latter provided with a groove 28 at its upper end part 29.

This groove is designed to cooperate with a complementary rib belonging to the blocking means 8, which will now be described.

Referring to FIGS. 3A and 3B, the means 8 comprise a rigid base body 31, for example made of titanium (said base body can also be made of a rigid plastic).

The body 31 extends about an axis 32. It is cylindrical and comprises, at its upper part 33, the complementary rib 34 designed to permit vertical blocking in the upward direction with the second orifice of the ring, while at the same time permitting a rotation of one with respect to the other.

Its lower part 35 is cylindrical and cooperates by friction (permitting a rotation about the axis 32) with the lower portion 26 of the second orifice of the ring.

The body 31 is provided with a through-orifice 36 of substantially oblong cross section.

The means 8 moreover comprise a component 37 which serves to hold the band 6 and which is made of plastic material and is at least partially wedge-shaped, that is to say with a prismatic or substantially prismatic shape.

The component 37 has a bore 38 running through it for the passage of the ends 6', 6" of the band, said bore 37 having a cross section that is deformable between a first cross section S1 for the free passage of the end portions when the component 37 is not inserted with real compression into the orifice (FIG. 3A), and a narrowed cross section S2 for blocking the end portions by compression when the component is inserted entirely into the orifice 36 (FIG. 3B).

More precisely, the component 37 has a first central part 39 with a horizontal cross section that is rectangular or substantially rectangular, and with a longitudinal vertical cross section with a shape that is an isosceles trapezoid or substantially an isosceles trapezoid with walls 40 symmetrical with respect to a longitudinal plane P, with the periphery uniformly toothed on the outside (teeth 41).

The teeth 41 (for example seven in number) are formed by longitudinal ridges of triangular shape, of which the vertices are directed upward or are horizontal, with an acute angle (imbricated).

The lower teeth or the lower tooth of the component and the one or more upper teeth of the orifice of the body form a means of pre-connection to each other by a snap-fit action.

The component 37 moreover has two end parts 42 of semicylindrical or substantially semicylindrical shape having walls of oval cross section which are symmetrical with respect to the plane perpendicular to the longitudinal plane P, the oval configuration of which is directed outward and, as will be seen, is designed to cooperate with opposite walls of the orifice 36.

The trapezoidal cross section has an angle at the base b (with respect to the small base of the trapezoid).

The bore 38 thus has a horizontal cross section of oblong shape, like a cat's tongue, which will deform between a sectional shape S1 (FIG. 3A) and a sectional shape S2 narrowed at the middle (FIG. 3B).

In the embodiment more particularly described here, the component 37 thus has a core 43 that is hollowed out by the bore 38 formed by the first central part 39 and the end parts 42.

It has the opposite main walls 40, of which the outer face is inclined and forms the wedge connected by the two rounded end walls 42 which are designed to cooperate with the orifice by friction, which will be described below.

The thickness e of the junctions 22 between main walls and end walls 42 is smaller (for example twice as thin) in order to permit the deformation by squeezing in the transverse direction without deformation in the longitudinal direction during the insertion of the component into the orifice (cf. FIG. 3B).

In the remainder of the description, the same reference numbers will be used to designate identical or similar elements.

FIG. 4 shows a system (without band) with pedicle screw 4, joining/guiding component 20, rod 3, compression screw 15, and upper part 12' of the body 9 different than that described with reference to FIGS. 1 and 1A.

Figure 5:
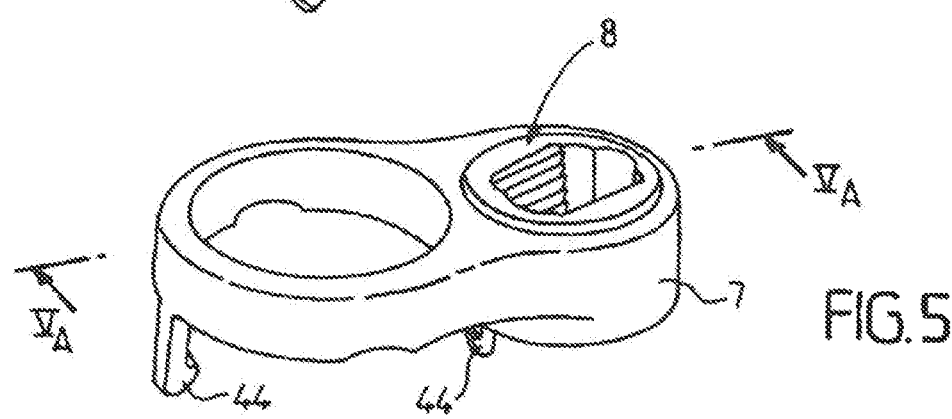
FIG. 5 is a perspective view of the ring used in the device in FIG. 4.
Figure 5A:
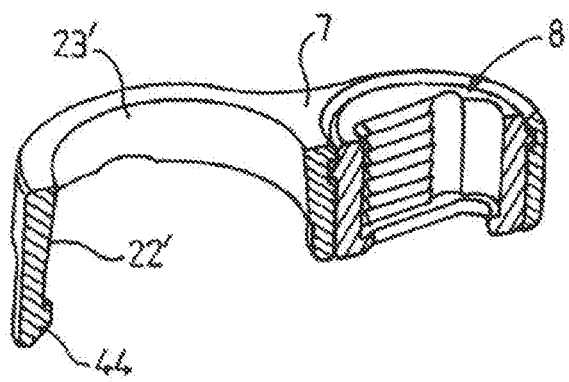
FIG. 5A is a sectional view along $V_A$-$V_A$ of the ring in FIG. 5.

Here, the junction between the outer wall of the upper part 12' of the lug and the inner wall of the bore of the first orifice 22' is frustoconical (small base toward the top), for example with friction of the Morse taper type. The ring 7 (cf. FIGS. 5 and 5A) comprises two deformable stubs 44 in the lower part of the orifice, which cooperate with the lower face 45 of a protruding lower part 46 of the upper part 12' with which they snap-fit, thereby fixing the ring on the lug.

Figure 6:
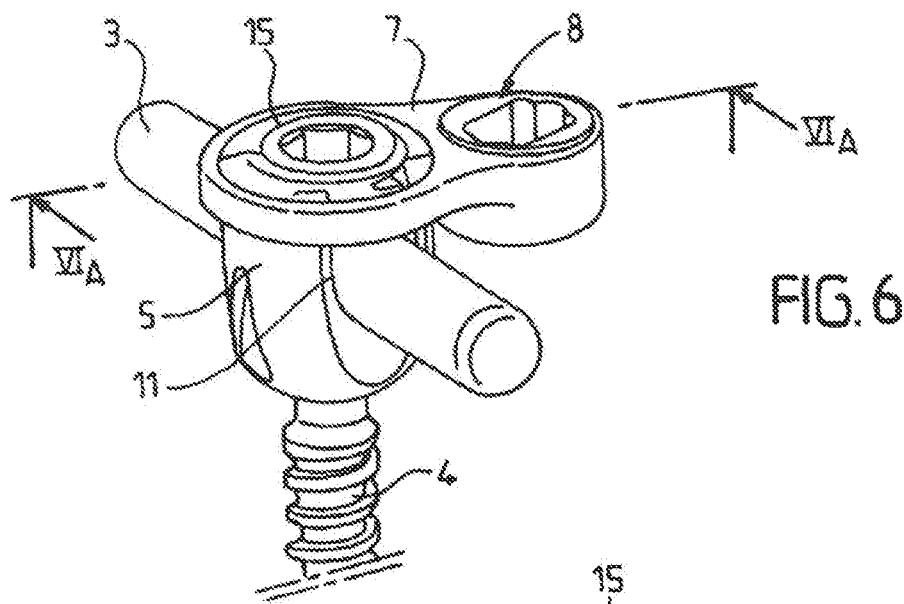
FIG. 6 is a partial perspective view of another embodiment of the upper part of a device according to the invention.
Figure 6A:
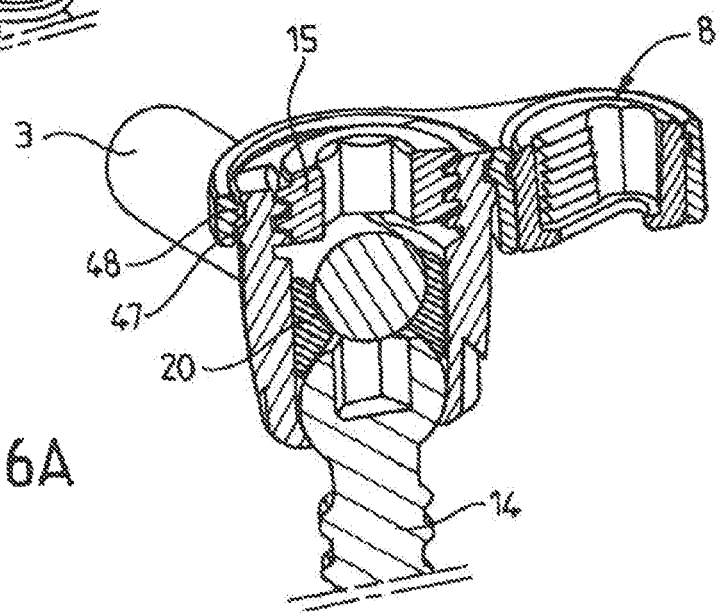
FIG. 6A is a perspective and sectional view along $VI_A$-$VI_A$ in FIG. 6.
Figure 7:
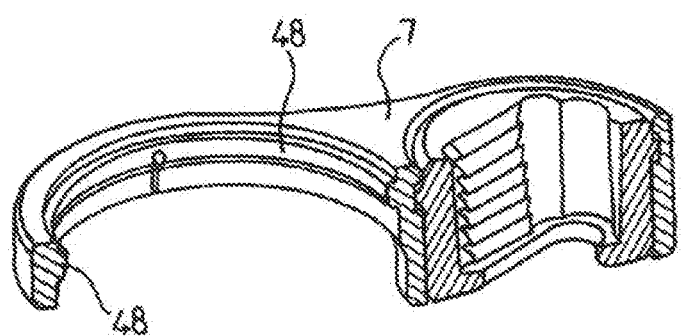
FIG. 7 is an enlarged sectional view of the ring in FIGS. 6 and 6A.

FIGS. 6, 6A and 7 show another embodiment of lug and ring according to the invention.

Here, the lug 5 comprises an upper part provided with a retention groove 47, and the first orifice 22 is provided with a rib of corresponding shape designed to be engaged with force one inside the other.

Figure 8:
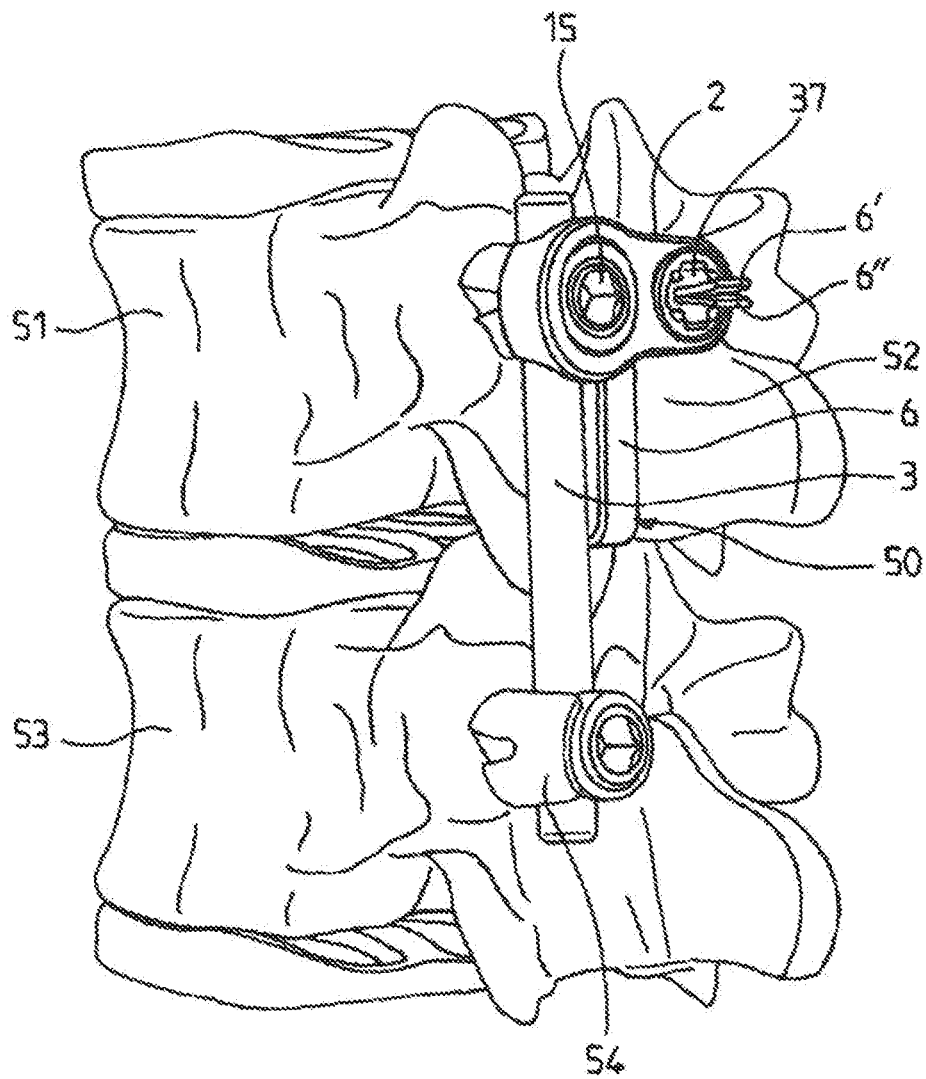
FIG. 8 is a perspective view of a system comprising a device according to an embodiment of the invention, with reference to FIG. 1, and a rod in position on the vertebrae.

FIG. 8 is a perspective view of a system 50 comprising a device 2 according to the embodiment of FIG. 1.

The device 2 is fixed in a vertebra 51 of poor quality, the fixation of which is assumed on the one hand by the pedicle screw, whose head is held on the rod 3 by screwing of the compression screw 15, and on the other hand by the band 6 passed around the epiphysis 52 of the vertebra 51.

The rod 3 is moreover fixed in a known manner to the adjacent vertebra 53 by a device 54 with a pedicle screw, in a manner know per se.

We will now describe, with reference to FIGS. 1, 3A, 3B and 8, the use of the system according to the embodiment of the invention more particularly described here.

Having screwed in the two pedicle screws, corresponding to the devices 2 and 54 provided with their respective lugs, into the adjacent vertebrae 51, 52, the surgeon inserts the rod 3 into the slots 11 of the lug heads, then clips on the ring provided with the blocking means, in which he has placed a first strand 6' of the band 6.

He then passes the flexible band (strand 6") around the vertebra and introduces it into the blocking means (that is to say into the holding component 37) and then tensions the band.

The free rotation of the component 37 makes it possible to avoid twisting of the band.

He then screws in the screw 15 for applying pressure to the rod, whereby the rod and the ring are then blocked against movement.

He then finishes tensioning the band 37.

Once the desired tensioning is achieved, the component 37 is introduced fully into the body 31, definitively blocking the two strands 6' and 6" by wedging.

As will be appreciated, and as is also apparent from the above, the present invention is not limited to the embodiments more particularly described. Instead, it includes all variants thereof, in particular those in which the blocking means are different and/or moreover comprise blocking ribs protruding inside the through-bore for blocking the strands 6' and 6".

The invention claimed is:

1. A device for fixing a spinal vertebra to a rod, comprising:
   a pedicle screw with a head;
   a lug for fixing the pedicle screw to the rod;
   a flexible band for connection to the vertebra;
   an attached ring rigidly connected to the lug, the lug being formed by a body rigidly connected to and forming a continuation of the head of the pedicle screw to which the ring is fixed; and
   blocking means rigidly connected to said ring for adjustably blocking the flexible band with respect to the lug, wherein the body is designed to be traversed laterally by the rod perpendicularly with respect to the pedicle screw, and is provided with an internal thread in its upper part, for fixing the rod by way of a compression screw, and wherein the ring comprises a first through-orifice which can be clipped by deformation onto an upper periphery of the lug, and a second lateral through-orifice which supports the blocking means and through which passes the band.

2. The device as claimed in claim 1, wherein the blocking means are movable in rotation with respect to the ring, whereby it is possible to avoid twisting of the band.

3. The device as claimed in claim 2, wherein the blocking means are inserted into the second through-orifice of the ring, which orifice is offset in relation to the pedicle screw and with which said blocking means cooperate by slight friction.

4. The device as claimed in claim 1, wherein the lug comprises an upper part which is cylindrical or shaped as a portion of a cylinder with a first diameter, and wherein the first through-orifice is cylindrical with a diameter matching the first diameter, with which it is designed to cooperate by friction, before the compression screw is screwed in, and to become blocked by slight expansion of the lug during the clamping.

5. The device as claimed in claim 1, wherein the lug comprises a frustoconical upper part, and wherein the first through-orifice having a frustoconical shape matching said upper part with which it cooperates by friction, and comprises at least one vertical blocking stub in a bottom portion.

6. The device as claimed in claim 1, wherein the lug comprises an upper part provided with a retaining groove or rib, and the first through-orifice of the ring is provided with a rib or groove of corresponding shape designed to be engaged with force one inside the other.

7. The device as claimed in claim 6, wherein the second through-orifice of the ring comprises a retaining rib or groove, and the blocking means comprise a holding component with a complementary groove or rib designed to be clipped then blocked vertically upward with the rib or groove of the second through-orifice of the ring.

8. The device as claimed in claim 1, wherein the blocking means comprise a rigid base body with a through-orifice, and a holding component that is insertable into said orifice, the holding component being at least partially in the shape of a squeezable wedge comprising a central bore for passage of opposite end portions of the band, said bore having a cross section that is deformable between a first cross section for free passage of the end portions when the component has not been inserted into the orifice, and a second cross section for blocking said end portions by compression when the component is entirely or substantially entirely inserted into the orifice.

9. The device as claimed in claim 1, wherein the head of the pedicle screw is a round or oblong, the head of the pedicle screw mounted pivotably in rotation in a lower part of the lug, and wherein the lug has a joining structure between a cylindrical wall of the rod and the head of said pedicle screw.

10. A system for fixing a spinal vertebra, having a rod and at least one device as claimed in claim 1.

11. A method for fixing a rod to a vertebra, in which a pedicle screw is screwed into the vertebra, the pedicle screw being provided with a lug for fixing the screw to the rod, the rod is slid through the lug, and a compression screw is screwed onto the rod through an upper part of the lug, wherein, before screwing in the compression screw, a flexible band is passed around said vertebra, a first through-orifice of a ring is clipped onto an upper periphery of the lug, said ring being able to be clipped or fixed by deformation on said upper periphery, said ring comprising a second lateral through-orifice for supporting adjustable means for blocking the flexible band, said blocking means being movable in rotation with respect to the ring and/or the lug, the flexible band is placed on the vertebra and in the blocking means, one starts to tension said flexible band, a free rotation making it possible to limit the twisting stresses of the band, after which one finishes tensioning the band before finally blocking the compression screw and the band with respect to the lug.

12. The method as claimed in claim 11, wherein, with the blocking means comprising a rigid base body with a through-orifice, and a holding component insertable into said orifice, the holding component being at least partially in the shape of a squeezable wedge comprising a central bore for passage of opposite end portions of the band, said bore having a cross section that is deformable between a first cross section for free passage of the end portions when the component has not been inserted into the orifice, and a second cross section for blocking said end portions by compression when the component is entirely or substantially entirely inserted into the orifice, the band is inserted into the base body and the holding component and, after tensioning, and in order to block the band against movement, the component is inserted entirely into the body.

* * * * *